United States Patent
Butt et al.

(10) Patent No.: US 8,962,200 B2
(45) Date of Patent: Feb. 24, 2015

(54) HUMIDITY MEASURING DEVICE AND METHOD

(75) Inventors: Shazad Butt, Troy, MI (US); Brian Rutkowski, Ypsilanti, MI (US); Jay Morley, Saginaw, MI (US); Mujeeb Ijaz, Ypsilanti, MI (US)

(73) Assignee: Ford Motor Company, Dearborn, MI (US)

( * ) Notice: Subject to any disclaimer, the term of this patent is extended or adjusted under 35 U.S.C. 154(b) by 1867 days.

(21) Appl. No.: 11/355,566

(22) Filed: Feb. 15, 2006

(65) Prior Publication Data

US 2007/0186619 A1 Aug. 16, 2007

(51) Int. Cl.
*H01M 8/04* (2006.01)
*G01N 25/56* (2006.01)
*G01N 7/00* (2006.01)
*G01N 33/00* (2006.01)

(52) U.S. Cl.
CPC ........... *G01N 25/56* (2013.01); *H01M 8/04089* (2013.01); *H01M 8/04126* (2013.01); *G01N 33/0016* (2013.01); *Y02E 60/50* (2013.01)
USPC .......................................... 429/413; 73/29.01

(58) Field of Classification Search
USPC ................................ 429/12–46, 413; 73/29.01
See application file for complete search history.

(56) References Cited

U.S. PATENT DOCUMENTS

| 3,771,349 | A | * | 11/1973 | Yatabe ..................... 73/29.05 |
| 3,811,951 | A | | 5/1974 | Stedman |
| 4,028,942 | A | * | 6/1977 | Gardiner .................. 73/335.02 |
| 4,131,011 | A | * | 12/1978 | Ling ......................... 73/29.01 |
| 5,190,726 | A | | 3/1993 | Shinoki et al. |
| 6,042,634 | A | * | 3/2000 | Van Tassel et al. ............. 95/14 |
| 6,706,430 | B2 | | 3/2004 | Wheat et al. |
| 6,821,660 | B2 | | 11/2004 | Andrews et al. |
| 2001/0045118 | A1 | * | 11/2001 | Lloyd et al. ..................... 73/1.06 |
| 2002/0009623 | A1 | * | 1/2002 | St-Pierre et al. ................ 429/13 |
| 2002/0031692 | A1 | * | 3/2002 | Fuglevand et al. ............. 429/22 |
| 2003/0064271 | A1 | | 4/2003 | Stenersen |
| 2003/0189416 | A1 | | 10/2003 | Scholta et al. |
| 2004/0185315 | A1 | | 9/2004 | Enjoji et al. |
| 2005/0053815 | A1 | | 3/2005 | Yang et al. |

* cited by examiner

*Primary Examiner* — Gregg Cantelmo
(74) *Attorney, Agent, or Firm* — Damian Porcari, Esq.; Tung & Associates

(57) ABSTRACT

A humidity measuring device is disclosed. The humidity measuring device includes a housing having a housing interior, a temperature controller thermally engaging the housing, a humidity sensor provided in the housing interior and an inlet conduit and an outlet conduit disposed in fluid communication with the housing interior. A fuel cell system and a method of measuring humidity in a gas stream are also disclosed.

16 Claims, 2 Drawing Sheets

HUMIDITY MEASURING DEVICE AND METHOD

FIELD

The present invention relates to apparatuses and methods for measuring the humidity of gases. More particularly, the present invention relates to a humidity measuring device and method which is suitable for accurately measuring the humidity of a gas stream in a fuel cell system or other application.

BACKGROUND

Currently, fuel cell systems use a polymer electrolyte membrane (PEM) having a polymer that requires the presence of water to transport protons harvested from hydrogen through the membrane. The water which is required for conduction of protons through the membrane is delivered to the membrane via humidified air and hydrogen gas streams. Insufficient humidification of the air and hydrogen streams leads to drying of the membrane, resulting in higher resistance to ion flow and reduced fuel cell performance. On the other hand, excessive humidification of the air and hydrogen streams can result in accumulation of water in the GDL (gas diffusion layer) of a fuel cell stack, resulting in flooding and covering of the active catalysts in the fuel cell membranes. This also reduces fuel cell performance. Therefore, humidity measurement would be beneficial in the air and hydrogen gas streams of a fuel cell system to measure the humidity of the air or gas, respectively.

Today's state-of-the-art humidity sensor technology typically does not provide a robust humidity measurement within a bi-phasic environment. For example, during a cold start of a fuel cell system, unprotected humidity sensors become saturated and report inaccurate readings as a result of liquid water contacting the humidity sensor. This occurs because the sensor is located in a condensing environment that contains high levels of liquid water.

SUMMARY

The present invention is generally directed to a humidity measuring device. The humidity measuring device includes a housing having a housing interior, a temperature controller thermally engaging the housing, a humidity sensor provided in the housing interior and an inlet conduit and an outlet conduit disposed in fluid communication with the housing interior.

The present invention is further generally directed to a fuel cell stack having at least one inlet and at least one outlet. At least one humidity measuring device is provided in fluid communication with at least one of the at least one inlet and the at least one outlet of the fuel cell stack. The at least one humidity measuring device comprises a housing having a housing interior provided in fluid communication with at least one of the at least one inlet and the at least one outlet of the fuel cell stack, a temperature controller thermally engaging the housing and a humidity sensor provided in the housing interior.

The present invention is further directed to a method of measuring humidity in a gas stream. The method includes providing a main stream of gas, diverting a slip stream from the main stream of gas, elevating a temperature of the slip stream relative to a temperature of the main stream and measuring a humidity of the slip stream.

BRIEF DESCRIPTION OF THE DRAWINGS

The invention will now be described, by way of example, with reference to the accompanying drawings, in which.

DETAILED DESCRIPTION

Figure 1:
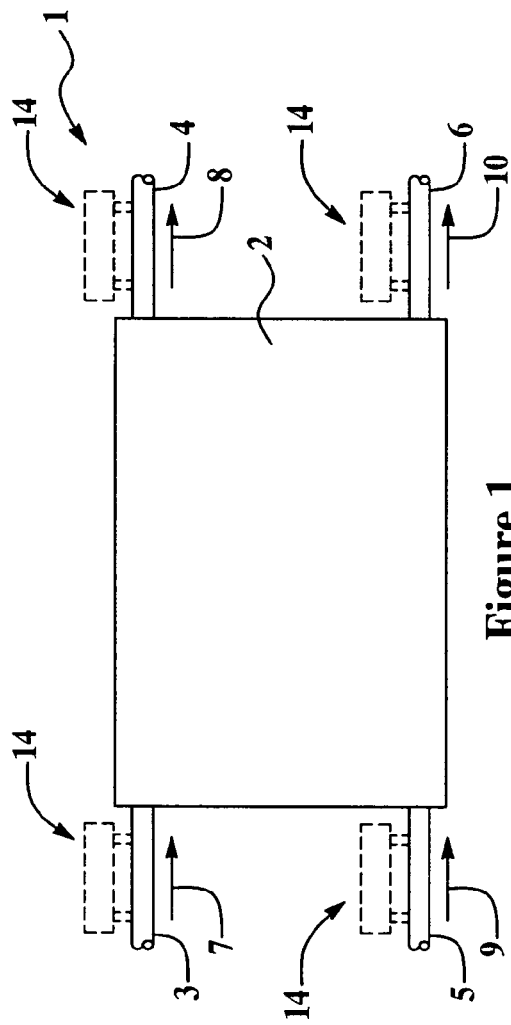
FIG. 1 is a schematic view of a fuel cell system in implementation of an illustrative embodiment of a humidity measuring device according to the present invention.

Referring to the drawings, a fuel cell system in implementation of an illustrative embodiment of a humidity measuring device according to the present invention is generally indicated by reference numeral 1 in FIG. 1. The fuel cell system 1 typically includes a fuel cell stack 2 having multiple polymer electrolyte membranes (PEMs) (not shown) each of which is positioned between an anode (not shown) and a cathode (not shown). A gas diffusion layer (GDL) (not shown) is provided between the PEM and the anode and between the PEM and the cathode. An anode inlet 3 and an anode outlet 4, as well as a cathode inlet 5 and a cathode outlet 6, are provided in fluid communication with the fuel cell stack 2. The anode inlet 3 is adapted to distribute an anode stream 7 which contains a fuel gas, such as hydrogen, into the fuel cell stack 2, whereas the anode outlet 4 is adapted to distribute an anode exhaust stream 8 from the fuel cell stack 2. The cathode inlet 5 is adapted to distribute a cathode stream 9 which contains an oxidant, such as air, into the fuel cell stack 2. The cathode outlet 6 is adapted to distribute a cathode exhaust stream 10 containing exhaust air and water vapor from the fuel cell stack 2. The invention is also applicable to measuring humidity of a stream of gas being fed into any type of system, such as an internal combustion engine or other engine, for example, instead of the fuel cell system 1.

In typical operation of the fuel cell system 1, at the anode (not shown), electrons are harvested from the hydrogen in the anode stream 7 and distributed through an external circuit (not shown) typically containing a motor (not shown). The protons from the hydrogen are conducted from the anode, through the PEM (not shown) to the cathode (not shown). At the cathode, electrons returning from the external circuit are combined with the protons to form water, which is distributed from the fuel cell stack 2 as the cathode exhaust 10. A humidity measuring device 14, the details of which will be hereinafter described, is provided in at least one of the anode inlet 3, the anode outlet 4, the cathode inlet 5 and the cathode outlet 6 to accurately measure the humidity in the anode stream 7, the anode exhaust 8, the cathode stream 9 and/or the cathode exhaust 10. Accordingly, the humidity measuring device 14 is adapted to accurately measure the humidity of the anode stream 7, anode exhaust stream 8, cathode stream 9 and/or cathode exhaust 10.

Figure 2:
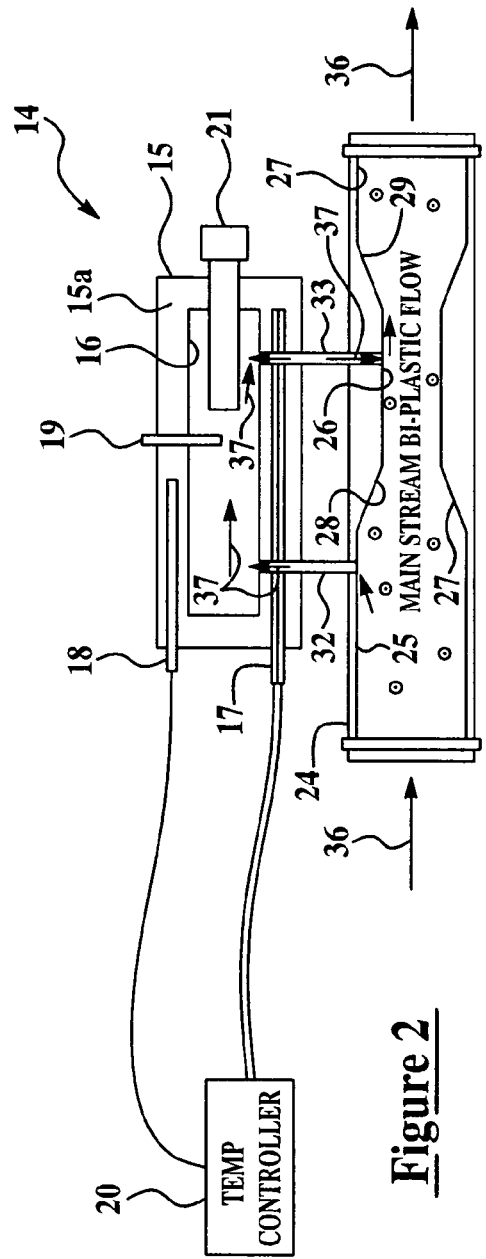
FIG. 2 is a schematic view of an illustrative embodiment of a humidity measuring device according to the present invention.

As shown in FIG. 2, the humidity measuring device 14 typically includes a housing 15 having a housing wall 15a which defines a housing interior 16. A gas flow conduit 24 is provided in fluid communication with the housing interior 16 of the housing 15 through a device inlet conduit 32 and a device outlet conduit 33. The gas flow conduit 24 may be, for example, an anode inlet 3, anode outlet 4, cathode inlet 5 and/or cathode outlet 6 of a fuel cell system 1. Alternatively, the gas flow conduit 24 may be a gas flow conduit in any type of system for the conveyance of a gas the humidity of which is to be measured.

A cartridge heater 17 may be provided in the portion of the housing wall 15a of the housing 15 which interfaces with the device inlet conduit 32 and device outlet conduit 33. A temperature controller 20 is connected to the cartridge heater 17 for controlling the temperature of the cartridge heater 17. The temperature controller 20 may be, for example, a regulating programmable thermal controller (PTC) heater or a coolant flow controller. A housing thermocouple 18 may further be provided in the housing wall 15a of the housing 15 and connected to the temperature controller 20. A gas thermocouple 19 may further be provided in the housing wall 15a and extend into the housing interior 16. The gas thermocouple 19 is connected to the temperature controller 20. Accordingly, by operation of the temperature controller 20, the temperature of the housing interior 16 can be controlled through the cartridge heater 17, housing thermocouple 18 and/or gas thermocouple 19. A humidity sensor 21 is further provided in the housing interior 16 and typically extends adjacent to the device outlet conduit 33. A microcontroller may be connected to or associated with the gas thermocouple 19 and humidity sensor 21 to calculate a dew point of a gas flowing through the housing 15.

As further shown in FIG. 2, the gas flow conduit 24 may have an inlet wall portion 25, a middle wall portion 26 having a diameter which is less than that of the inlet wall portion 25 and an outlet wall portion 27, having a diameter which is greater than that of the middle wall portion 26. A narrowing transition wall portion 28 may extend between the inlet wall portion 25 and the middle wall portion 26, and a widening transition wall portion 29 may extend between the middle wall portion 26 and the outlet wall portion 27. The device inlet conduit 32 exits the gas flow conduit 24 at the inlet wall portion 25, whereas the device outlet conduit 33 enters the gas flow conduit 24 at the middle wall portion 26.

In typical use of the humidity measuring device 14, a main stream 36 of a gas flows through the gas flow conduit 24 in the direction shown by the arrow 36 in FIG. 2. The main stream 36 may be that of an anode stream 7, anode exhaust 8, cathode stream 9 or a cathode exhaust 10 in the operation of the fuel cell system 1, for example, and is a biphasic gas stream including water and gas. Alternatively, the main stream 36 may be a stream of gas in any type of application or system in which the humidity of the gas is to be accurately measured. The temperature of the main stream 36 is a selected temperature. For example, in the case of an anode stream 7 or cathode stream 9 in the operation of a fuel cell system 1, the temperature of the main stream 36 may be about 68° C., for example. The temperature of the housing interior 16 is maintained at a higher temperature than that of the main stream 36, by operation of the temperature controller 20. For example, in operation of a fuel cell system 1, the temperature of the housing interior 16 may be about 75° C.

As the main stream 36 flows through the gas flow conduit 24, the pressure of the main stream 36 is higher between the inlet wall portion 25 and the middle wall portion 26 of the gas flow conduit 24 than in the housing interior 16 of the housing 15. Conversely, the pressure of the main stream 36 in the middle wall portion 26 of the gas flow conduit 24 is lower than in the housing interior 16 of the housing 15. Therefore, a slip stream 37 is diverted from the main stream 36 and through the device inlet conduit 32, housing interior 16 of the housing 15, device outlet conduit 33 and back into the gas flow conduit 24, respectively. The remaining portion of the main stream 36 flows through the gas flow conduit 24, bypassing the device inlet conduit 32.

As it flows through the housing interior 16, the slip stream 37 contacts the humidity sensor 21, which measures the humidity of the slip stream 37. In the housing interior 16, the slip stream 37 is heated to a temperature which prevents condensation of the moisture in the slip stream 37 onto the interior surfaces of the housing interior 16 and the humidity sensor 21. Therefore, moisture is prevented from condensing on the humidity sensor 21, such that the humidity sensor 21 is capable of obtaining an accurate measurement of the level of humidity in the slip stream 37, and therefore, in the main stream 36. As it re-enters the gas flow conduit 24 from the device outlet conduit 33, the slip stream 37 joins the main stream 36. The gas flow conduit 24 distributes the main stream 36 into the fuel cell stack 2 (in the case of the anode inlet 3 or cathode inlet 5) or from the fuel stack 2 (in the case of the anode outlet 4 or cathode outlet 6). The shape of the interior surfaces of the gas flow conduit 24 minimizes or optimizes the flow rate of the slip stream 37 to prevent liquid water in the main stream 36 from entering the slip stream 37 as a result of non-sufficient force.

Figure 3:
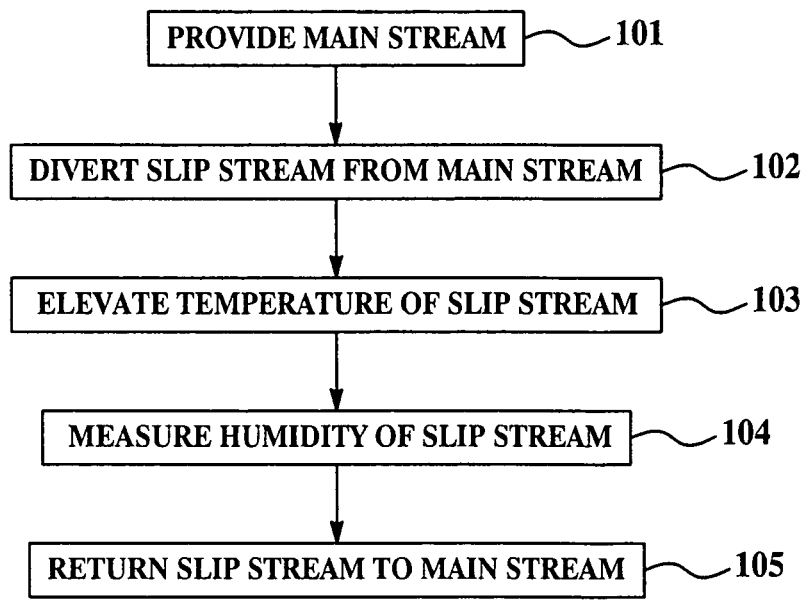
FIG. 3 is a flow diagram illustrating a method of measuring humidity in a gas stream according to an illustrative embodiment of the present invention.

Referring next to the flow diagram of FIG. 3, a method of measuring humidity in a gas stream according to an illustrative embodiment of the present invention is shown. In step 101, a main stream of a biphasic gas which contains moisture is provided. The main stream of gas may be, for example, an anode stream, a cathode stream, an anode exhaust or a cathode exhaust of a fuel cell system. In step 102, a slip stream is diverted from the main stream. In step 103, the slip stream is heated to a temperature which exceeds that of the main stream. In step 104, the humidity of the slip stream is measured. The water in the slip stream remains in the vapor phase, such that the water does not condense onto a humidity sensor which measures the humidity of the slip stream. This enhances the accuracy of the humidity sensor in measuring the humidity level of the slip stream, and therefore, the main stream. In step 105, the slip stream may be returned to the main stream. Alternatively, the slip stream may be discharged to the environment or atmosphere. The method may further include measuring the temperature of the slip stream and using humidity and temperature of the slip stream to calculate a dewpoint of the main stream. Furthermore, a main stream temperature sensor may be provided in the main stream and a relative humidity of the main stream determined using the dew point.

While the preferred embodiments of the invention have been described above, it will be recognized and understood that various modifications can be made in the invention and the appended claims are intended to cover all such modifications which may fall within the spirit and scope of the invention.

What is claimed is:

1. A fuel cell system, comprising:
a fuel cell stack having at least one inlet and at least one outlet;
at least one humidity measuring device provided in fluid communication with at least one of said at least one inlet and said at least one outlet of said fuel cell stack; and
wherein said at least one humidity measuring device comprises a housing having a housing interior provided in fluid communication by an inlet conduit and an outlet conduit with said at least one of said at least one inlet and said at least one outlet of said fuel cell stack, a temperature controller thermally engaging said housing and a humidity sensor provided in said housing interior, wherein said humidity sensor is provided within said housing interior, said humidity sensor extending adjacent to and spaced apart from an opening of said outlet conduit within said housing interior, wherein a respective distal end of said inlet conduit and said outlet conduit each connect with a respective orifice disposed in a wall portion of a gas flow conduit comprising said at least one inlet and said at least one outlet of said fuel cell stack, wherein each of said respective orifices opens into said gas flow conduit.

2. The fuel cell system of claim 1 wherein said at least one of said at least one inlet and said at least one outlet comprises a gas flow conduit including an inlet wall portion having a first diameter and a middle wall portion having a second diameter less than said first diameter, and wherein said inlet conduit is connected to said inlet wall portion and said outlet conduit is connected to said middle wall portion.

3. The fuel cell system of claim 2 wherein said gas flow conduit comprises an outlet wall portion having a third diameter greater than said second diameter.

4. The fuel cell system of claim 3 further comprising a first transition wall portion between said inlet wall portion and said middle wall portion and a second transition wall portion between said middle wall portion and said outlet wall portion.

5. The fuel cell system of claim 1 further comprising a heater thermally engaging said housing and connected to said temperature controller.

6. The fuel cell system of claim 5 further comprising a housing thermocouple thermally engaging said housing and connected to said temperature controller.

7. The fuel cell system of claim 6 further comprising a gas thermocouple extending into said housing interior and a microcontroller associated with said humidity sensor and said gas thermocouple, said microcontroller configured to determine a dew point of a sampled gas stream from said fuel cell stack.

8. The fuel cell system of claim 1, wherein said inlet conduit and said outlet conduit each communicate with said housing interior on a common side of said housing.

9. The fuel cell system of claim 1, wherein said humidity sensor is disposed within said housing interior relatively closer to said opening of said outlet conduit compared to an opening of said inlet conduit within said housing interior.

10. A fuel cell system, comprising:
  a fuel cell stack having at least one inlet and at least one outlet;
  at least one humidity measuring device provided in fluid communication with at least one of said at least one inlet and said at least one outlet of said fuel cell stack; and
  wherein said at least one humidity measuring device comprises a housing having a housing interior provided in fluid communication by an inlet conduit and an outlet conduit with said at least one of said at least one inlet and said at least one outlet of said fuel cell stack, a temperature controller thermally engaging said housing and a humidity sensor provided in said housing interior, wherein said humidity sensor is provided within said housing interior said humidity sensor extending adjacent to and spaced apart from an opening of said outlet conduit within said housing interior, wherein a respective distal end of said inlet conduit and said outlet conduit each connect with a respective orifice disposed in a wall portion of gas flow conduit comprising said at least one inlet and said at least one outlet. of said fuel cell stack, wherein each of said respective orifices opens into said gas flow conduit; and,
  a gas thermocouple extending into said housing interior and a microcontroller associated with said humidity sensor and said gas thermocouple, said microcontroller configured to calculate a dew point of a sampled gas stream from said fuel cell stack.

11. The fuel cell system of claim 10 wherein said at least one of said at least one inlet and said at least one outlet comprises a gas flow conduit including an inlet wall portion having a first diameter and a middle wall portion having a second diameter less than said first diameter, and wherein said inlet conduit is connected to said inlet wall portion and said outlet conduit is connected to said middle wall portion.

12. The fuel cell system of claim 11 wherein said gas flow conduit comprises an outlet wall portion having a third diameter greater than said second diameter.

13. The fuel cell system of claim 12 further comprising a first transition wall portion between said inlet wall portion and said middle wall portion and a second transition wall portion between said middle wall portion and said outlet wall portion.

14. The fuel cell system of claim 10 further comprising a heater and a housing thermocouple thermally engaging said housing and connected to said temperature controller.

15. The fuel cell system of claim 10, wherein said inlet conduit and said outlet conduit each communicate with said housing interior on a common side of said housing.

16. The fuel cell system of claim 10, wherein said humidity sensor is disposed within said housing interior relatively closer to said opening of said outlet conduit compared to an opening of said inlet conduit within said housing interior.

* * * * *